(12) United States Patent
McNeely et al.

(10) Patent No.: US 6,591,852 B1
(45) Date of Patent: Jul. 15, 2003

(54) FLUID CIRCUIT COMPONENTS BASED UPON PASSIVE FLUID DYNAMICS

(75) Inventors: Michael R. McNeely, Sandy, UT (US); Mark K. Spute, Salt Lake City, UT (US); Arnold R. Oliphant, Poway, CA (US)

(73) Assignee: BioMicro Systems, Inc., Salt Lake City, UT (US)

( * ) Notice: Subject to any disclaimer, the term of this patent is extended or adjusted under 35 U.S.C. 154(b) by 0 days.

(21) Appl. No.: 10/060,442

(22) Filed: Jan. 30, 2002

Related U.S. Application Data

(63) Continuation-in-part of application No. 09/967,402, filed on Sep. 27, 2001, which is a continuation of application No. 09/417,691, filed on Oct. 13, 1999, now Pat. No. 6,296,020

(60) Provisional application No. 60/103,970, filed on Oct. 13, 1998, and provisional application No. 60/138,092, filed on Jun. 8, 1999.

(51) Int. Cl.$^7$ .............................. F15B 21/00; F17D 1/18
(52) U.S. Cl. ..................... 137/14; 137/806; 137/833; 137/841; 204/601
(58) Field of Search ................... 137/806, 833, 137/841, 14; 204/601

(56) References Cited

U.S. PATENT DOCUMENTS

| | | | | |
|---|---|---|---|---|
| 3,191,623 A | * | 6/1965 | Bowles | 137/833 |
| 3,327,726 A | | 6/1967 | Hatch, Jr. | 137/806 |
| 3,417,770 A | | 12/1968 | Denlson | 137/806 |
| 3,799,742 A | | 3/1974 | Coleman | |
| 3,993,062 A | | 11/1976 | Jess | 128/214 |
| 4,426,451 A | | 1/1984 | Columbus | |
| 4,549,574 A | * | 10/1985 | Taylor | 137/565 |
| 4,618,476 A | | 10/1986 | Columbus | 422/100 |
| 4,676,274 A | * | 6/1987 | Brown | 137/806 |
| 4,756,884 A | | 7/1988 | Hillman et al. | |

(List continued on next page.)

FOREIGN PATENT DOCUMENTS

| | | |
|---|---|---|
| WO | WO 97/02357 | 1/1997 |
| WO | WO 98/29736 | 7/1998 |
| WO | WO 98/56505 | 12/1998 |
| WO | 0933126 A1 | 8/1999 |

(List continued on next page.)

OTHER PUBLICATIONS

Duffy, David C., et al., "Microfabricated Centrifugal Microfluidic Systems: Characterization and Multiple Enzymatic Assays," Analytical Chemistry, vol. 71, No. 20., Oct. 15, 1999, 4669–4678.

(List continued on next page.)

*Primary Examiner*—A. Michael Chambers
(74) *Attorney, Agent, or Firm*—Madson & Metcalf

(57) ABSTRACT

Methods and apparatus for controlling fluid flow through microchannels by use of passive valves or stopping means comprised of abrupt microchannel widenings in the microchannels are presented. Such passive fluid flow barriers create pressure barriers impeding flow of solution past the passive fluid flow barriers until enough force is built up to overcome the force of the pressure barrier. Use of such stopping means acting as passive barriers or valves allows the flow of fluids through microchannels to be regulated so as to allow fluids to be mixed or diluted after being introduced via a single channel, or to be split into multiple channels without the need for individual pipetting. Flow through the multiple channels can be regulated to allow a series of sister wells or chambers to all fill prior to the fluid flowing beyond any one of the sister wells or chambers. The filling of sister wells or chambers in this manner allows all wells or chambers to undergo reactions in unison. The use of air ducts in microchannels to prevent trapping of air in the microchannels is also presented.

52 Claims, 10 Drawing Sheets

U.S. PATENT DOCUMENTS

| | | | |
|---|---|---|---|
| 4,868,129 A | 9/1989 | Gibbons et al. | |
| 4,946,795 A | 8/1990 | Gibbons et al. | |
| 4,963,498 A | 10/1990 | Hillman et al. | 436/69 |
| 5,051,182 A | 9/1991 | Wang et al. | 210/500.27 |
| 5,077,017 A | 12/1991 | Gorin et al. | |
| 5,104,813 A | 4/1992 | Besemer et al. | |
| 5,119,116 A | 6/1992 | Yu | 346/140 |
| 5,223,219 A | 6/1993 | Subramanian et al. | |
| 5,230,866 A | 7/1993 | Shartle et al. | |
| 5,304,487 A | 4/1994 | Wilding et al. | 435/291 |
| 5,378,504 A | 1/1995 | Bayard et al. | 426/377 |
| 5,427,946 A | 6/1995 | Kricka et al. | 435/291 |
| 5,486,335 A | 1/1996 | Wilding et al. | 422/55 |
| 5,498,392 A | 3/1996 | Wilding et al. | 422/68.1 |
| 5,587,128 A | 12/1996 | Wilding et al. | 422/50 |
| 5,635,358 A | 6/1997 | Wilding et al. | 435/7.2 |
| 5,637,469 A | 6/1997 | Wilding et al. | 435/7.21 |
| 5,726,026 A | 3/1998 | Wilding et al. | 435/7.21 |
| 5,726,404 A | 3/1998 | Brody | 200/81 R |
| 5,730,187 A | 3/1998 | Howitz et al. | 137/833 |
| 5,846,396 A | 12/1998 | Zanzucchi et al. | |
| 5,856,174 A | 1/1999 | Lipshutz et al. | 435/286.5 |
| 5,866,345 A | 2/1999 | Wilding et al. | 435/7.21 |
| 5,869,004 A | 2/1999 | Parce et al. | 422/100 |
| 5,900,130 A | 5/1999 | Benvegnu et al. | 204/453 |
| 5,910,287 A | 6/1999 | Cassin et al. | |
| 5,922,591 A | 7/1999 | Anderson et al. | 435/287 |
| 5,922,604 A | 7/1999 | Stapleton et al. | 436/46 |
| 5,928,880 A | 7/1999 | Wilding et al. | 435/7.21 |
| 5,955,029 A | 9/1999 | Wilding et al. | 422/68.1 |
| 5,958,344 A | 9/1999 | Levine et al. | |
| 5,976,336 A | 11/1999 | Dubrow et al. | 204/453 |
| 5,980,719 A | 11/1999 | Cherukuri et al. | |
| 5,992,820 A | 11/1999 | Fare et al. | |
| 6,004,515 A | 12/1999 | Parce et al. | 422/100 |
| 6,043,080 A | 3/2000 | Lipshutz et al. | 435/287.2 |
| 6,046,056 A | 4/2000 | Parce et al. | 436/514 |
| 6,048,498 A | 4/2000 | Kennedy | 422/99 |
| 6,068,752 A | 5/2000 | Dubrow et al. | 204/604 |
| 6,086,740 A | 7/2000 | Kennedy | 204/601 |
| 6,086,825 A | 7/2000 | Sundberg et al. | 422/100 |
| 6,193,471 B1 | 2/2001 | Paul | 417/53 |
| 6,296,020 B1 | 10/2001 | McNeely et al. | 137/806 |

FOREIGN PATENT DOCUMENTS

| | | |
|---|---|---|
| WO | WO 99/56954 | 11/1999 |
| WO | WO 99/64836 | 12/1999 |
| WO | WO 00/21659 | 4/2000 |
| WO | 1016864 A2 | 7/2000 |
| WO | WO 01/41931 | 6/2001 |
| WO | WO 01/88525 | 11/2001 |
| WO | WO 01/90614 | 11/2001 |

OTHER PUBLICATIONS

Man, P.F., et al., "Microfabricated Capillarity–Driven Stop Valve and Sample Injector." University of Michigan.

Anderson, Rolfe C. et al., "Advances in Integrated Genetic Analysis," Affymetrix, Inc.

"Recent Patent in Microfabrication and Microfluidics", Nature Biotechnology, vol. 17, Jun. 1999, p. 606.

Anderson, R. C. et al., "Microfluidic Biochemical Analysis System," Int. Cong. On Soild–State Sens. and Act Transducers, 1997, Chicago, Jun. 16–19, 1997, 477–480.

Brahmasandra, S.N. et al., "A Microfabricated Fluidic Reaction and Separation System for Integrated DNA Analysis," Micro Total Analysis Systems, 1998, D.J. Harrison and A. Van Den Berg. Eds Kluwer Acad Publ. Dordrecht (1998) Proceedings of the $\mu$TAS 1998 Workshop, Banff, Canada, Oct. 13–16, 1998, 307–310 and cover page.

Lee, L.P. et al., "Key Elements of Tranparent Teflon Microfluidic System," Micro Total Analysis Systems 1998, D.J. Harrison and A. Van den Berg, eds. Kluwer Acad. Publ. Dordrecht (1998); Proceedings of the $\mu$TAS 1998 Workshop, Banff,Canada, Oct. 13–16, 1998, 245–48, cover page.

Banerjee, "Structured custom design for LOC applications.," ASME Microfluidics for Lab–on–Chip (LOC) Pre–Seminar Workshop, Sep. 9, 2001.

Zeng, Jun, et al., "Design Analyses of Capillary Burst Valves in Centrifugal Microfluidics," Technical Proceeding of mTAS (Micro analysis systems) May 2000 conference, Ensched, The Netherlands, pp. 493–496.

* cited by examiner

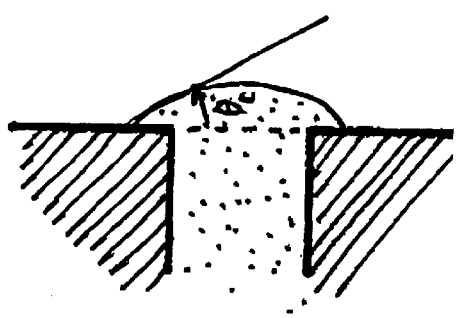
FIG. 1E
FIG. 1F
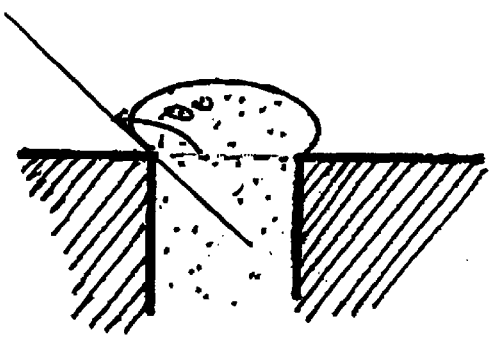
FIG. 1I
FIG. 1J
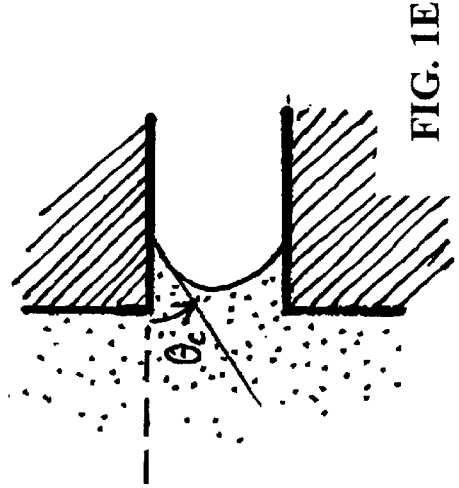
FIG. 1G
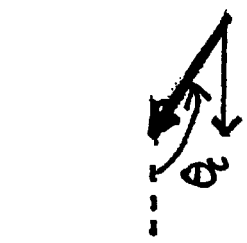
FIG. 1H
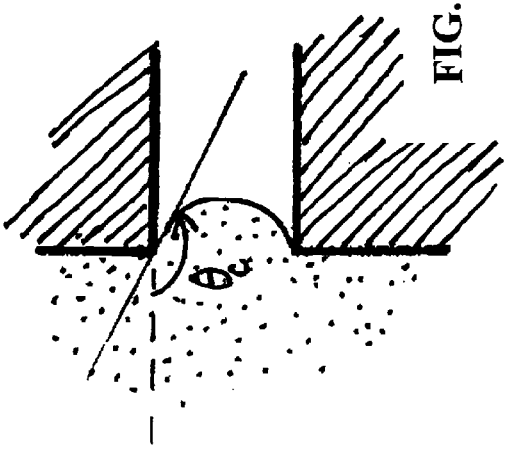
FIG. 1K
FIG. 1L

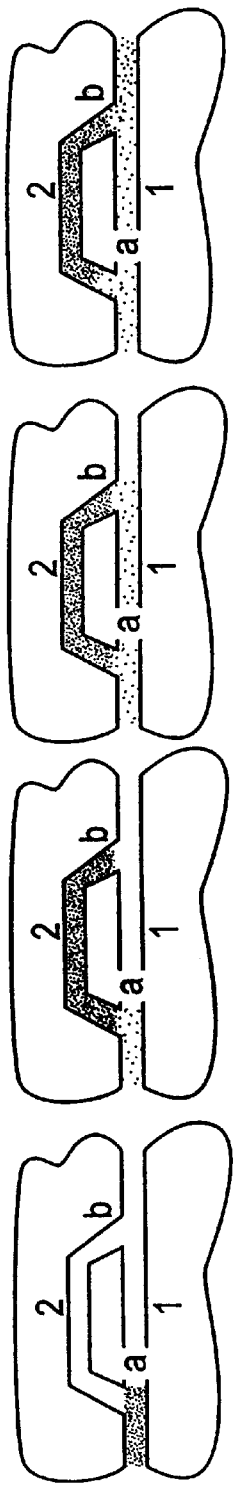
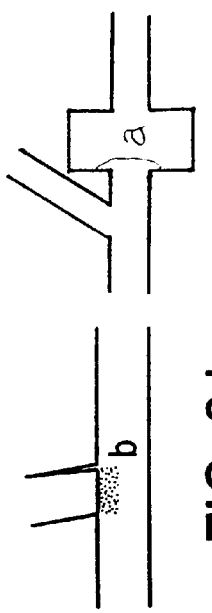

FLUID CIRCUIT COMPONENTS BASED UPON PASSIVE FLUID DYNAMICS

RELATED APPLICATIONS

This application is a continuation-in-part of U.S. patent application Ser. No. 09/967,402, filed Sep. 27, 2001; which is a continuation of U.S. application Ser. No. 09/417,691, filed Oct. 13, 1999, now U.S. Pat. No. 6,296,020, which claims the benefit of U.S. Provisional Application No. 60/103,970, filed on Oct. 13, 1998, and U.S. Provisional Application No. 60/138,092, filed on Jun. 8, 1999, each of the foregoing is incorporated herein by reference.

BACKGROUND OF THE INVENTION

1. Field of the Invention

The present invention relates to methods and apparatus for passively controlling fluid flow through microchannels. More specifically, the present invention relates to passive stopping means in a microfluidic circuit that act as pressure barriers to impede and direct the flow of fluid through microchannels, and methods for their use.

2. Description of Related Art

Controlling the movement of fluids through channels on a micro scale has important applications in a number of technologies. For example, in the field of molecular biology, polymerase chain reactions (PCR) have been performed in a chip containing microfabricated flow channels (U.S. Pat. Nos. 5,498,392; 5,587,128; 5,726,026). In the electronics field, thermal ink jet printers use printheads with microchannels through which ink must flow in a well-controlled manner (U.S. Pat. No. 5,119,116). Proper control of fluids through microchannels has been a challenge, because microdimensions impart characteristics and behaviors that are not found in larger scale systems, which are due primarily to the greater influence of surface effects.

The term "surface effects" is used to describe specific characteristics of a surface on a micro scale. Materials often have unbound electrons, exposed polar molecules, or other molecular level features that generate a surface charge or reactivity characteristic. Due to scaling, these surface effects or surface forces are substantially more pronounced in microstructures than they are in traditionally sized devices. This is particularly true in micro scale fluid handling systems where the dynamics of fluid movement are governed by external pressures and by attractions and repulsions between liquids and the materials of the microfluidic systems through which they flow.

Many micro scale fluid handling systems suffer from uneven and irregular fluid flow. Many such problems are due to surface effects such as those mentioned above. It is frequently the case that microscale fluid handling systems are designed to perform multiple fluid handling steps in parallel. However, some microscale fluid systems fill unevenly. In others, channels fill at different rates. Additionally, some fluid circuits that split samples into multiple reaction chambers may do so unevenly. Those combining samples from multiple reaction chambers may do so incompletely or unevenly. Such problems may result in incomplete assays or assays conducted with insufficient amounts of reagent or sample. Some of these problems may result in differences in the reaction times for the different assays, thus changing the results. These and other problems may affect the accuracy of assays and the usability of the microscale fluid handling systems themselves.

Accordingly, a need becomes apparent for fluid circuits in which fluid flow may be regulated. Technologies for actively regulating the flow of fluid through fluid circuits are generally not favored due to their complexity and cost. Thus, a need specifically exists for fluid circuits that allow for the passive regulation of fluid flow internally. This could be accomplished by providing fluid circuits comprising passive stopping means for acting as pressure barriers to regulate the flow of fluid through microchannels. Such fluid circuits and methods for their use are disclosed herein.

SUMMARY OF THE INVENTION

The apparatus of the present invention has been developed in response to the present state of the art, and in particular, in response to the problems and needs in the art that have not yet been fully solved by currently available microscale fluid handling systems, also called microfluidics systems.

Thus, the present invention discloses means of controlling the flow of fluids through microchannels in a manner to allow mixing or diluting of the fluids and/or separation of the fluids or a fluid into several channels for multiprocessing. It also discloses various means for consolidating or combining several samples or channels into a smaller number of samples or channels, and the use of air escape channels and stopping means to facilitate complicated fluid processing. The flow of fluid through the microchannels is primarily controlled by structures that act as passive fluid flow barriers, which in the present invention are abrupt microchannel widenings purposely formed into the microchannels by micromachining or other manufacturing techniques. Abrupt microchannel widenings include short, low volume, widenings, i.e., a restricted region of a microchannel having an increased diameter, being short enough that the widening does not significantly increase the overall volume of the channel; longer widenings, as occur when a channel enters a well or chamber; step changes in channel diameter, i.e., points where a smaller diameter channel joins a larger diameter channel; and even points where a channel enters a substantially "unbounded" space, i.e., the channel opens to the exterior surface of the microfluidic device. These passive fluid flow barriers or abrupt microchannel widenings act to stop fluid flow by creating a passive pressure barrier that may be overcome by sufficient pressure, or by wetting both sides of the barrier. Passive fluid flow barriers can be produced by abrupt microchannel widenings in both hydrophilic and hydrophobic materials.

Unlike flow barriers that require moving parts, the passive fluid flow barriers or abrupt microchannel widenings can be static and their operation does not depend upon the use of moving parts. They are thus cheaper and simpler to construct than the various types of microelectromechanical active valves, and they do not require external controls.

Passive flow barriers formed by abrupt microchannel widenings may be used in microfluidic circuits in combination with other types of passive fluid flow barriers, which may include hydrophobic channel widenings, microchannel regions having modified surface properties (e.g., regions where the contact angle or the surface tension has been modified, e.g., by including films of salts or surfactants or by a hydrophobic patch in an otherwise hydrophilic channel, or vice versa).

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof, which are illustrated, in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 1A–L illustrate the concept of hydrophilicity and hydrophobicity. FIG. 1A shows the relation between σ (surface tension) and $\theta_c$ (the contact angle between the meniscus of fluid and the wall of a channel). FIG. 1B illustrates the meniscus formed when hydrophilic tubing draws water into it. FIG. 1C illustrates the meniscus formed when a hydrophobic tubing pushes water away from the tubing. FIG. 1D illustrates a channel narrowing for passively controlling fluids in either hydrophobic or hydrophilic materials. FIG. 1E diagrammatically illustrates a fluid entering a hydrophilic channel. FIG. 1F shows the surface tension forces on the fluid of FIG. 1E. FIG. 1G shows fluid entering a hydrophobic channel. FIG. 1H shows the forces exerted on the fluid of FIG. 1G. FIG. 1I illustrates a fluid exiting a hydrophilic channel. FIG. 1J shows the surface tension forces present on the fluid in FIG. 1I. FIG. 1K shows a fluid exiting a hydrophobic channel. FIG. 1L shows the forces exerted on the fluid in FIG. 1K.

FIGS. 2A–L illustrate a method of mixing two fluids together using a branching system of microchannels that join together. The channels include stopping means at points 'a' and 'b' to control the flow of fluid. Both fluids enter serially through a single common channel and are mixed subsequent to point 'b'. FIGS. 2E–L illustrate the structure of the stopping means and the position of fluid at the stopping means whether the stopping means is a hydrophobic restriction, hydrophilic restriction, a hydrophobic patch or a salt patch.

FIGS. 3E–I illustrate different configurations of the stopping means, depending on which type is being employed.

FIGS. 4A–G illustrate the presence of air or a gas which can be trapped in a series of hydrophobic microchannels and the use of a vent to allow the air or gas to escape while preventing fluid through the vent. FIGS. 4E–G illustrate alternative stopping means that allow air to escape if the fluid channels are not hydrophobic.

DETAILED DESCRIPTION OF THE PREFERRED EMBODIMENTS

Figure 1A:
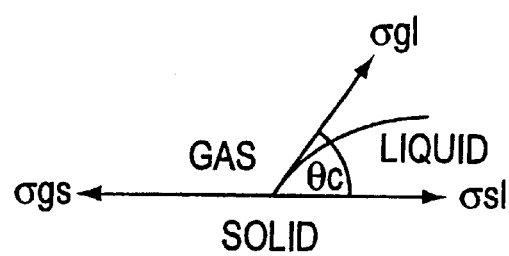

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 11, is not intended to limit the scope of the invention, as claimed, but is merely representative of presently preferred embodiments of the invention.

This invention deals with the passive control of fluids within microfluidic circuits. This passive control may be generated by using natural forces that exist on a micro scale. Specifically, capillarity, which is caused by the attraction or repulsion of a fluid toward certain materials, allows passive control of fluid flow in the fluid circuits of the invention. Herein, the terms passive fluid flow barrier, passive fluid valve, abrupt microchannel widening, stopping means, are used to denote structures which stop fluid flow through a microchannel by generating a passive pressure barrier, Passive fluid flow barriers may be produced in a variety of ways, including channel surface modifications, abrupt channel narrowings (in hydrophobic materials if a polar fluid is used, or in hydrophilic materials if a non-polar fluid is used), or channel widenings (in both hydrophilic and hydrophobic materials). An equation useful for determining the passive fluid flow barriers generated by modifying parameters of channel radius, contact angle, and surface tension, as well as various microfluidic circuit structures based thereon, are presented in commonly owned U.S. Pat. No. 6,296,020, incorporated herein by reference. The present invention represents particular applications of the invention of U.S. Pat. No. 6,296,020. Disclosed are passive fluid flow barriers produced by long or short abrupt channel widenings, as well as passive fluid flow barriers formed at inlets to structures such as chambers and wells, and openings from a microchannel to the outside of the microfluidic circuit.

The purpose of the invention is to stop fluid flow along one path in a circuit until enough pressure is applied to the fluid to push it past the passive fluid valve, or until the passive fluid valve itself is removed or made insignificant. The pressure barrier that is generated by the passive fluid valve can be utilized to direct fluid through the circuit in some creative manner, or to hold fluid at a specific location. As briefly noted above, the capillary properties of materials used in microfluidic, or fluid, circuits give rise to the passive fluid flow barriers of the invention.

Capillarity is usually represented by the equation $h=2\sigma_{gl}\cos(\theta_c)/\text{grp}$. This equation describes the height (or depth), h, of a fluid within a capillary tube compared to the level of the fluid outside the capillary tube. $\theta_c$, or the contact angle of the fluid with the capillary tube material, governs whether the fluid in the tube is above or below the level of the fluid outside the tube. If this contact angle of the capillary tube material is less than 90° with respect to the fluid, the material is considered hydrophilic (water liking). If the contact angle of the tube material is greater than 90° with respect to the fluid, the material is considered hydrophobic (water fearing). The term $\sigma_{gl}$ represents the surface tension of the fluid with respect to the ambient (usually air, measured in millijoules/m$^2$), while g is the gravitational constant (m/s$^2$), r is the radius of the capillary tube (m), and $\rho$ is the fluid density (kg/m$^3$).

Figure 1B:
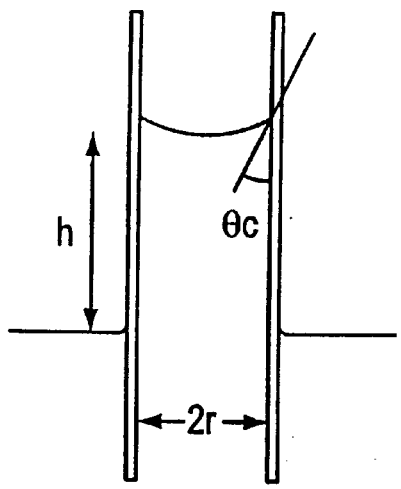
Figure 1C:
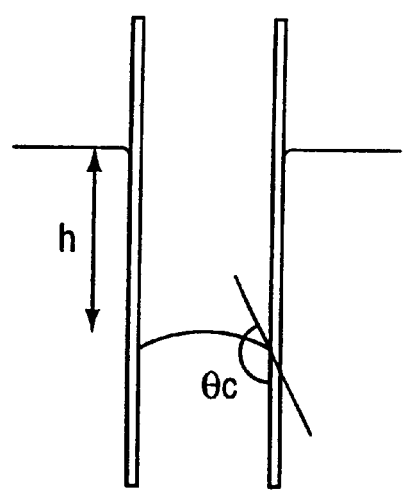

FIGS. 1A–C illustrate the concepts of hydrophilicity and hydrophobicity. FIG. 1A illustrates $\theta_c$. $\sigma_{gs}$ is the surface tension between a gas and a solid, $\sigma_{sl}$ is the surface tension between a solid and a liquid, and $\sigma_{gl}$ is the surface tension between a gas and a liquid. $\sigma_{gs}=\sigma_{sl}+\sigma_{gl}\cos(\theta_c)$. $\theta_c$ (angle in degrees) for water on various materials at around 20° C. is shown in Table 1. FIG. 1B illustrates that hydrophilic tubing, such as glass, draws water into the tube. FIG. 1C is similar to FIG. 1B but illustrates that the use of hydrophobic tubing (such as Teflon®) pushes water away from the tube.

TABLE 1

$\theta_c$ for Selected Materials

| Material | $\theta_c$ |
|---|---|
| Glass | 0 |
| Acetal | 60 |
| Polystyrene | 84 |
| HDPE (high density polyethylene) | 87.1 |
| PVDF (polyvinylidene fluoride) | 94.8 |
| PTFE (polytetrafluoroethylene) | 104 |
| FEP (fluorinated ethylenepropylene) | 111 |

The term $\rho gh$, from the equation for capillarity, is sometimes referred to as the pressure head of a fluid, P (Pa). Re-writing the capillarity equation with respect to P gives $P=2\sigma_{gl}\cos(\theta_c)/r$. In order to effect a stopping means, $\sigma_{gl}$, $\theta_c$, r, or a combination of any of the three, needs to change from one side of the stopping means to the other. This will generate a pressure barrier, which causes the fluid to stop until the pressure barrier is overcome or removed. For example, if the radius of a channel were changed in order to effect a stopping means, the equation describing the pressure required to push past the stopping means would be given by $P=2\sigma_{gl}\cos(\theta_c)(1/r_1-1/r_2)$, where $r_1$ is the radius of the channel before the stopping means and $r_2$ is the radius of the channel after the stopping means. This equation is a simplification of the physical system that may be present. A true model would take into consideration the actual channel geometries and other physical/chemical characteristics.

Figure 1D:
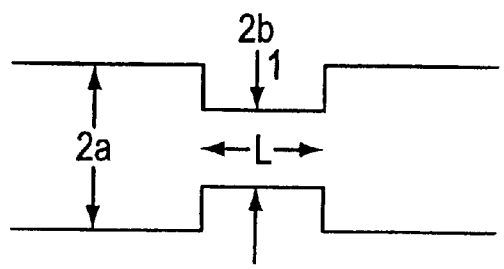

FIG. 1D illustrates a change in channel radius. Specifically, a channel of radius "a" changes abruptly to a channel of a smaller radius "b." The channel of radius b again changes abruptly to the larger channel of radius a. For either hydrophilic or hydrophobic materials, a stopping means or pressure barrier would be produced at the point where the channel radius increases in size. In this instance $r_1$ would be given by b and $r_2$ would be given by a. This would generate a positive value for P, because the cosine of angles between 0 and 90 degrees (the contact angle of the material) is positive. A positive P suggests a pressure barrier. If the material were hydrophobic, a stopping means would be produced at the point where the channel decreases in size. In this case $r_1$ would be given by a, and $r_2$ by b. A negative cosine value, due to a contact angle greater than 90 degrees, would be multiplied by a negative ($1/r_1-1/r_2$) term, resulting in a positive P, or a pressure barrier.

If the contact angle of the material were to change, such as a hydrophilic channel having a hydrophobic region, this can also provide a stopping means. This situation would be characterized by the equation $P=2\sigma_{gl}[\cos(\theta_{c1})-\cos(\theta_{c2})]/r$, where $\theta_{c1}$ is the contact angle of the material before the stopping means (hydrophilic) and $\theta_{c2}$ is the contact angle of the material after the stopping means (hydrophobic). A negative cosine of $\theta_{c2}$ would result in a positive P, signifying a pressure barrier.

A change in surface tension of a fluid flowing through a microfluidic circuit, such as by lining the channel walls with absorbable salts or surfactants, could also generate a stopping means. The equation describing such a pressure barrier would be given by $P=2\cos(\theta_c)(\sigma_{gl1}\sigma_{gl2})/r$, where $\sigma_{gl1}$ is the surface tension of a fluid before the stopping means and $\sigma_{gl2}$ is the surface tension of the fluid after the stopping means. In a hydrophobic material the surface tension would need to increase across the stopping means in order to create a pressure barrier.

This invention deals with the passive control of fluids through microfluidic channels using the stopping means described in the previous paragraphs. More specifically, the stopping means of the present invention is derived by abruptly increasing the radius or cross-sectional flow area of a flow. Although discussion is focused on aqueous (polar) fluids, passive fluid control structures discussed herein can be used in connection with non-polar fluids as well. Although passive fluid flow barriers can be formed in either hydrophilic or hydrophobic materials, as will be discussed in greater detail below, it will often be the case that such passive fluid flow barriers are used in microfluidic circuits that include other types of passive fluid flow barriers as well. Therefore, a variety of combinations of channel materials and fluids may be used to achieve the desired effect of controlling fluid flow via the use of either abrupt channel widening or narrowings within microchannels, as passive fluid control structures. The following are some examples of such useful combinations:

(A) PTFE (Teflon® or polytetrafluoroethylene), FEP (fluorinated ethylenepropylene), PFA (perfluoroalkoxy alkane) or PVDF (polyvinylidene fluoride) as the channel material and polar solutions such as water, saline or buffer solutions not possessing a significant percentage of surfactants, this percentage being known or easily determined by one of skill in the art.

(B) Metals, glass, PMMA (polymethylmethacrylate), polycarbonate, Nylon 6/12 or PVC (polyvinylchloride) as the channel material and non-polar solutions such as hexane, heptane, toluene or benzene.

(C) PTFE, FEP, PFA of PVDF as the channel material with a hydrophilic coating such as Elastophilic™ and non-polar solutions such as those mentioned in (B).

(D) Metals, glass, PMMA, polycarbonate, Nylon 6/12 or PVC as the channel material with a hydrophobic coating such as Teflon® AF and polar solutions such as those mentioned in (A).

In devices in which passive fluid flow barriers are formed by abrupt channel widenings, but not by channel restrictions, the pairing of fluid and substrate material would not be as critical, and other combinations, including, for example, hydrophobic material and non-polar fluid, or hydrophilic material and aqueous fluid, could be used.

Passive valving relies upon the fact that the developing flow of a fluid stream requires extra pressure, or work, or energy, to go through a stopping means, and that it would, therefore, preferentially take a path of lesser resistance or stop altogether until enough pressure is built up to force the fluid through the stopping means. Developing flow is defined as an advancing stream of fluid that possesses a moving interface of solution and air or some other gas. The point of interface is defined as the meniscus. Another characteristic of developing flow is that the surfaces of the flow chamber in front of, or downstream of, the advancing meniscus are not significantly wetted with the fluid that is flowing. Established flow, on the other hand, is where there is no moving meniscus and where all surfaces of the flow channels are significantly wetted.

As noted above, passive valving technology is in part based on the principle that fluid flow is impeded by certain changes in the capillary forces in narrow channels, and that at a given pressure level, it is possible to stop fluid flow by putting either a narrowing or widening in a channel. This is formalized in the following equation, which is presented in the issued U.S. Pat. No. 6,296,020 (Column 2, line 35):

$$\Delta P = 2\sigma_{gl} \cos\theta_c \left[ \frac{1}{r_1} - \frac{1}{r_2} \right] \qquad \text{EQN. 1}$$

In the equation, $\Delta P$ is used to denote the minimum pressure differential required to move fluid in a channel past a change in channel radius. Further, $r_1$ denotes the channel radius before the stopping means (or radius change), and $r_2$ denotes the channel radius after the stopping means. Additionally, $\sigma_{gl}$ is the surface tension of the fluid with respect to the ambient gaseous phase (typically air), and $\theta_c$ is the contact angle of the fluid on the channel surface. The change in channel radius is also frequently referred to as a "stopping means" since most often the change in radius is used to generate a "stopping means."

As disclosed in U.S. Pat. No. 6,296,020 and reviewed below, depending on the channel material and the relative values of $r_1$ and $r_2$, the change in channel radius may draw fluid into the channel, rather than impede its flow. When the channel radius changes from a larger value to a smaller value, $(1/r_1-1/r_2)$ is negative, while it is positive when the channel radius changes from a smaller to a larger value. For hydrophilic materials, $0°<\theta_c<90°$, so $\cos(\theta_c)$ is positive, and in order to generate a pressure barrier or stopping means (positive $\Delta P$), $r_1$ must be $<r_2$. For hydrophobic materials, $90°<\theta_c<180°$, so $\cos(\theta_c)$ is negative, and $\Delta P$ is positive when $r_1>r_2$.

EQN. 1 can also be applied to larger changes in channel radius, such as instances where a channel exits or enters a chamber or well, or where a microchannel is widened. If the chamber has a radius $r_1$ that is large relative to the channel radius $r_2$, then the term depending on the channel radius predominates, and the term depending on the chamber radius approaches zero. In other words, for the case where fluid is entering a channel from a chamber, $r_1>>r_2$, EQN. 1 can be rewritten:

$$\Delta P = 2\sigma_{gl} \cos\theta_c \left[ -\frac{1}{r_2} \right] = -2\sigma_{gl} \cos\theta_c \left[ \frac{1}{r_2} \right] \qquad \text{EQN. 2}$$

In FIG. 1E, fluid is shown entering a hydrophilic channel. In 1F, the heavy arrow illustrates the forces on the fluid due to surface tension. The lighter arrow in FIG. 1F illustrates the component of the force in the direction parallel to the channel. It can be seen that the component of the force in the direction parallel to the channel is related to the total force by a factor of $\cos(\theta_c)$. In this case $(1/r_1-1/r_2)$ is negative and $\cos(\theta_c)$ is positive, so $\Delta P$ is negative, meaning a negative pressure gradient must be applied to oppose the surface tension component parallel to the channel, which tends to draw the fluid into channel.

FIG. 1G illustrates fluid entering a hydrophobic channel. The force on the fluid due to surface tension, which, as before, is related to the total force by a factor of $\cos(\theta_c)$, is shown in FIG. 1H. In this case, $(1/r_1-1/r_2)$ is negative, as before, but $\cos(\theta_c)$ is negative, because $90<\theta_c<180°$. Thus, $\Delta P$ is positive, meaning that the positive pressure gradient must be applied to move fluid into the channel.

Applying EQN. 1 to the case where fluid is exiting a channel and entering a chamber, well, or microchannel widening, $r_1<<r_2$, so $1/r_2$ approaches zero and $(1/r_1-1/r_2)$ is positive. However, a further modification must be made to EQN. 1 to take into account the fact that when fluid exits a channel into a large diameter chamber, the liquid-gas-solid interface occurs on the surface of the chamber just outside the exit of the chamber, rather than on the interior surface of the channel. This is illustrated in FIG. 1I for the hydrophilic case and FIG. 1J for the hydrophobic case. Since it is assumed that $r_1<<r_2$, it follows that the surface of the chamber is substantially perpendicular to the direction of the channel. The contact angle $\theta_c$, which is characteristic of the particular combination of gas, liquid and solid being used, would then be obtained by a measurement made with respect to the chamber surface, rather than the channel surface, as shown in FIG. 1I. However, in order to obtain the component of surface tension force in the direction parallel to the channel, as shown in FIG. 1J, the angle of the tension must be determined relative to the surface of the channel.

As shown in FIGS. 1I and 1J (for hydrophobic material) and FIGS. 1K and 1L (for hydrophilic material), a shifted contact angle, measured with respect to the interior of the channel, is indicated by $\theta_c'$. The shifted contact angle $\theta_c'$, equals $\theta_c-90°$.

The equation then becomes:

$$\Delta P = 2\sigma_{gl} \cos(\theta_c - 90°) \left[ \frac{1}{r_1} \right] = 2\sigma_{gl} \sin(\theta_c) \left[ \frac{1}{r_1} \right] \qquad \text{EQN. 3}$$

EQN. 3 is thus simply EQN. 1 applied to the situation that where $r_1<<r_2$. For hydrophilic materials, $0°<\theta_c<90°$, and for hydrophobic materials, $90°<\theta_c<180°$, so $\cos(\theta_c-90°)=\sin(\theta_c)$ will be positive. $1/r_1$ will also be positive, so a positive value of $\Delta P$ will be obtained, for both hydrophobic and hydrophilic materials, meaning that a positive pressure differential must be applied to overcome the force due to surface tension, i.e., a pressure barrier will be produced in both hydrophobic and hydrophilic materials. The effect predicted by EQN. 3 has been observed experimentally in microfluidic circuits configured according to the invention.

The scope of this invention is the use of various stopping means that are designed to control the flow of fluid in a network of fluid channels. More specifically this invention details the use of stopping means such as passive fluid flow barriers or microchannel widenings that create barriers to fluid flow as a fluid in a fluid circuit exits a narrow channel (either hydrophilic or hydrophobic) into an open space having a significantly larger diameter than the channel, such as, for example, a chamber. This means is defined using adapted versions of the equation used to describe other passive valving technologies.

The publications and other materials used herein to illuminate the background of the invention or provide additional details respecting the practice, are incorporated by reference, and for convenience are respectively grouped in the appended List of References.

The invention is a method of using passive stopping means in microchannels to control the flow of fluids through the microchannels. A microchannel is defined herein to be a channel having a diameter of from 0.1 to 5000 microns, and more preferably from 0.1 to 1000 microns. Advantage is taken of the surface effects between a fluid and the walls of the container holding the fluid. These surface effects come into play at the micro scale. The stopping means are designed to impede the flow of fluids under certain conditions thereby allowing control of the fluid. These stopping means act as passive valves because they regulate fluid flow but do not move.

An example of the effect of surface forces is capillarity. Capillarity, or capillary action, is demonstrated when water is drawn up into an open glass capillary tube without any outside pressure being applied. This is caused by the surface tension forces between the water and the glass surface, which pull water into the capillary tube. The narrower the capillary tube the greater the effect of the force that pulls the water into the tube. One physical parameter that characterizes the magnitude of the capillary force is the contact angle between the water and the glass. For contact angles less than 90°, the material, e.g., glass, is considered to be hydrophilic and water is drawn up into the tube. When the material has a contact angle greater than 90° it is considered to be hydrophobic. In the hydrophobic case extra pressure is required to push water into an open tube. The narrower the tube, the greater the force that is required to push water into the open tube. In both cases, however, once water has been introduced into the tube, the flow rates of the water are dependent more on pressure gradients and friction than on whether the material is hydrophobic or hydrophilic.

A stopping means such as a passive fluid flow barrier is generated by altering the character of a microchannel in such a way as to generate a pressure barrier. A pressure barrier is made by creating an abrupt change in the capillary force a fluid experiences while flowing through a microchannel. Such abrupt changes in capillary force may be made by changing the diameter of the microchannel the fluid is flowing through, by changing the contact angle of the microchannel material, by changing the surface tension of the flowing fluid, or by a combination of these methods.

In hydrophobic or hydrophilic materials, a pressure barrier may be generated by increasing the diameter of the flow channel. This may be accomplished by abruptly increasing the radius of the flow channel or opening the microchannel into a chamber or well. To practice this invention, the first microchannel, herein also referred to as the inlet of the passive fluid flow barrier, has a radius $r_1$, which is sufficiently small to enjoy capillary effects. The inlet radius $r_1$ may be from about 0.1 to about 5000 $\mu$m in size, and more preferably from about 0.1 to about 1000 $\mu$m. The microchannel widening, passive fluid flow barrier, chamber, or well into which the inlet flows has a radius $r_2$. In this configuration, the radius $r_1$ is sufficiently smaller than the radius $r_2$ to create a passive pressure barrier to cause fluid that is advancing through the fluid circuit of which these elements are a part to flow into an adjoining microchannel connected upstream of said passive pressure barrier rather than to flow past said barrier. In specific embodiments of the invention, radius $r_2$ is greater than about 1.5 times radius $r_1$. Alternatively, radius $r_2$ may be greater than about two times radius $r_1$. In yet other embodiments, radius $r_2$ may be greater than about three times radius $r_1$. In still other embodiments, radius $r_2$ may be greater than about five times radius $r_1$. Additionally, the radius $r_2$ may be greater than about ten times radius $r_1$. There appears to be no upper limit for how much larger $r_2$ can be than $r_1$, and thus exits from a microchannel to the exterior of the fluid circuit may also serve as passive fluid flow barriers.

A passive valve or fluid flow barrier can obtained with a long, large-volume, channel widening such as a chamber or well, or a short, low-volume, channel widening, such as a section of channel with a diameter of perhaps 2–3 times the diameter of the adjoining portions of the channel and a length that is about the same as the diameter of the adjoining portions of the channel. The low-volume channel widening can be used as a passive valve in a variety of fluid circuits, and is not limited to controlling the filling of chambers or wells. A channel opening to the outside of a device (rather than to an enclosed chamber, well, or channel) would also have this passive valving effect. Abrupt channel widenings can be used as a fluid control element in any of the fluid circuit structures disclosed in connection with other types of passive valves, including branching systems of channels for dividing fluids, or merging channels for mixing or combining fluids.

In non-wetted fluid circuits comprising said passive fluid flow barriers, the fluid circuit may additionally include secondary microchannels that also include passive fluid flow barriers that create passive pressure barriers in relation to fluid advancing through the fluid circuit. Such individual passive fluid flow barriers can be tuned to be of a different strength from each of the others. Such a configuration could dictate an order in which each secondary microchannel will fill. Additionally, one or more of these secondary microchannels may comprise a vent.

Fluid circuits having such passive fluid flow barriers based upon the abrupt increases in the radius of a microchannel may be created in many configurations. In some, the microchannels form a treelike or a fractal branching. As briefly noted above, the passive fluid flow barriers of the invention may comprise either a hydrophilic or a hydrophobic surface.

In a specific embodiment of non-wetted fluid circuits incorporating passive fluid flow barriers of the invention, the fluid circuit comprises a plurality of connected microchannels, wherein a passive fluid flow barrier exists within one or more of said microchannels, and wherein the passive fluid flow barrier comprises an inlet having a radius $r_1$ and an outlet having a radius $r_2$, wherein $r_1$ is sufficiently smaller than $r_2$ to create a passive pressure barrier causing fluid that is advancing through said fluid circuit to flow in an adjoining microchannel connected upstream of said passive fluid flow barrier rather than to flow past said passive fluid flow barrier, wherein at least one of said microchannels branches at a first point into an adjoining microchannel which rejoins said one of said microchannels at a second point and wherein said adjoining microchannel comprises a second passive fluid flow barrier immediately upstream of said second point. Such fluid circuits may include microchannels that form a treelike or a fractal branching. Additionally, such fluid circuits may further include one or more ports allowing a gas to enter into said fluid circuit. These ports may be large enough to allow gas to pass through said ports but small enough to prevent fluids from passing through said ports at a specific operating pressure. Alternatively, the ports may allow a fluid under pressure to enter into the fluid circuit. In other fluid circuits, one or more wells or chambers may be joined to a common consolidation well or chamber by one or more microchannels, thus allowing use of the fluid circuit to merge the fluids in the various microchannels.

Other fluid circuits of the invention may include a first microchannel and a second microchannel, in which the second microchannel branches from the first microchannel at a first intersection and rejoins the first microchannel at a second intersection, wherein the second microchannel has a first passive fluid flow barrier comprising a first abrupt microchannel widening at the first intersection and a second passive fluid flow barrier comprising a second abrupt microchannel widening at the second intersection. In such fluid circuits the second passive fluid flow barrier creates a greater pressure barrier than the first passive fluid flow barrier. Such fluid circuits may further comprise a vent between the first passive fluid flow barrier and the second passive fluid flow barrier.

In such fluid circuits, the first abrupt microchannel widening may comprise a chamber or well between the first intersection and the second intersection. In these fluid circuits the first abrupt microchannel widening may comprise a chamber or well at the second intersection.

Several methods may be utilized in practicing the invention of the application. One such is a method of moving a first fluid through a fluid circuit embodying the invention by forcing a second fluid under pressure through said one or more ports, said second fluid thereby forcing said first fluid to move through the passive pressure barrier of said fluid circuit by overcoming it with sufficient pressure.

In another, a method for mixing a first fluid and a second fluid within a non-wetted fluid circuit comprises the steps of inserting said first fluid into a main microchannel of the fluid circuit, wherein the first fluid is forced to flow into a first microchannel of the circuit of a known volume by a first abrupt microchannel widening within the main microchannel, and wherein the first microchannel comprises a second abrupt microchannel widening that creates a pressure barrier stronger than the first abrupt microchannel widening, wherein the first fluid is of an amount substantially equal to the volume of the first microchannel, and inserting the second fluid into said main microchannel of the fluid circuit, wherein the second fluid is forced past the first abrupt microchannel widening into a second microchannel, and the first microchannel and the second microchannel converge at the second abrupt microchannel widening at which point the first fluid and the second fluid will mix upon continued insertion of the second fluid or application of a force causing the first and second fluids to move. In this method, the fluid circuit may additionally comprise a vent. In fluid circuits including the stopping means of the invention, the first abrupt microchannel widening and said second abrupt microchannel widening are capillary barriers selected from the group of chambers, wells, long channel widenings, and short channel widenings.

These microfluidic circuits may be used to control fluid flow when they comprise at least two connected microchannels, each said microchannel containing a passive fluid flow barrier that creates a fluid pressure barrier. Such a method comprises the steps of stopping advancing fluid in a first microchannel by causing it to engage with a first passive fluid flow barrier, thereby directing fluid into a connected neighboring second microchannel until it engages a second passive fluid flow barrier, applying pressure to said fluid sufficient to overcome one of the first and second passive fluid flow barriers. One of the first and second passive fluid flow barriers must be weaker than the other, and the weaker fluid flow barrier will be overcome first to permit fluid to flow through to downstream portions of the microfluidic circuit. The first passive fluid flow barrier and the second passive fluid flow barrier are capillary barriers that each have an inlet and an outlet, wherein the inlet is sufficiently smaller than the outlet to create a fluid pressure barrier according to the present invention.

The outlet of each of the first and the second passive fluid flow barriers is defined by a radius ($r_2$ in the equations) which is at least about two times the size of a radius ($r_1$ in the equations) which defines the inlet of each of the first and the second passive fluid flow barriers. Alternatively, the outlet of each of the first and the second passive fluid flow barriers is defined by a radius that is at least about five times the size of a radius that defines the inlet of each of the first and the second passive fluid flow barriers. In the method, the second microchannel may branch from the first microchannel at a point immediately upstream of the first passive fluid flow barrier, or it may branch from the first microchannel at some distance upstream of the first passive fluid flow barrier. Additionally, the first and second passive fluid flow barriers may each open into a well or chamber. Further, in fluid circuits associated with such methods, the fluid circuit may comprise one or more wells or chambers joined to a common consolidation well or chamber by one or more microchannels. Additionally, the fluid circuit may include one or more air vents.

Fluid circuits incorporating passive fluid flow barriers according to the invention may be also used in a method of distributing a fluid from one channel to multiple wells, chambers or channels of the non-wetted fluid circuit. This method comprises the steps of passing the fluid from the one channel to branching channels leading to a first set of wells, chambers or channels, wherein the first set of wells, chambers or channels comprises a first passive fluid flow barrier within each well, chamber or channel that creates a fluid pressure barrier causing wells, chambers or channels upstream of the first passive fluid flow barrier to fill prior to the fluid moving to a second set of wells, chambers or channels, wherein the second set of wells, chambers or channels comprises a second passive fluid flow barrier within each well, chamber or channel that creates a fluid pressure barrier that is stronger than the fluid pressure barrier created by the first passive fluid flow barriers, wherein the first passive fluid flow barriers comprise the channel opening into the first set of wells, chambers, or channels; and causing fluid to push past the first passive fluid flow barriers within the first set of wells, chambers or channels and to stop at the second passive fluid flow barriers within the second set of wells, chambers or channels.

The fluid circuits may also be used in methods of controlling fluid flow through a non-wetted fluid circuit comprising at least two connected microchannels, wherein each said microchannel contains a passive fluid flow barrier that creates a fluid pressure barrier. Such methods comprise the steps of stopping advancing fluid in a first microchannel with a first passive fluid flow barrier, thereby directing fluid into a connected neighboring second microchannel, wherein the first passive fluid flow barrier comprises an inlet having a radius $r_1$ and an outlet having a radius $r_2$, wherein $r_1$ is sufficiently smaller than $r_2$ to create a passive pressure barrier causing fluid that is advancing through said fluid circuit to stop at said first passive fluid flow barrier; and overcoming the pressure barrier of the first passive fluid flow barrier by the advancing fluid engaging a second passive fluid flow barrier in the second microchannel, wherein the second passive fluid flow barrier creates a stronger pressure barrier than the first passive fluid flow barrier. In these fluid circuits, the second passive fluid flow barrier comprises an inlet having a radius $r_1$ and an outlet having a radius $r_2$, wherein $r_1$ is sufficiently smaller than $r_2$ to create a passive pressure barrier greater than the first passive fluid flow barrier. Further, the second microchannel may branch from the first microchannel at a point immediately upstream of the first passive fluid flow barrier, and the fluid circuit may comprise one or more wells and chambers.

Pressure barriers may be created in a hydrophobic material alternatively by decreasing the diameter of the flow channel. This restriction (a narrowing) should be sufficient to cause fluid to flow in alternate channels having a diameter greater than the restriction means. A narrowing of a channel can be effected by different means. For example, a channel of otherwise constant diameter can have a bump or ridge at one or more points that cause a narrowing just at those points. Another alternative is a channel of one diameter narrowing suddenly to a channel of a smaller diameter, i.e., a wide channel narrowing to a less wide channel. The magnitude of the pressure barrier that is generated is proportional to the narrowness of the restriction compared to the narrowness of the channel prior to the restriction. A short restriction will have minimal effect on fluid flow once flow is established through the restriction. It is preferred that the restriction be 1–1000 $\mu$m long, more preferably 5–500 $\mu$m long, and most preferably 10–300 $\mu$m long.

In a hydrophilic material a pressure barrier can also be generated by a channel restriction, similar to the method described for a hydrophobic material. However, in this case the fluid will not want to exit a restriction, due to the capillary forces that are holding it there. The magnitude of the pressure barrier that is generated is proportional to the narrowness of the restriction compared to the narrowness of the channel after the restriction. A short restriction will have minimal effect on fluid flow once flow is established through the restriction.

Also, in a hydrophilic material, a pressure barrier can be generated by changing the contact angle of the flow channel. Microfabrication techniques, for example, allow for the precise application of thin films of various materials that have a wide range of contact angles. The magnitude of the pressure barrier that is generated is proportional to the difference in the cosines of the contact angles of the materials comprising the stopping means.

A passive stopping means can also be generated by changing the surface tension of the fluid within the microchannel. This, also, could be realized by utilizing microfabrication techniques to deposit thin films of various salts or surfactants that are absorbed into the fluid. The magnitude of the pressure barrier that is generated is proportional to the difference in the surface tensions of the fluid on each side of the stopping means.

It is advantageous to use passive fluid dynamics to control the flow of fluid in micro channels or sets of micro channels. For example, if two daughter channels branch off of a main channel, a stopping means in one of the channels may encourage the fluid to flow in the channel with no stopping means. However, once the fluid has pushed past the stopping means, the stopping means, if designed properly, should have negligible effect on the established flow within the channels. In this case the stopping means acts as a passive valve.

The use of microchannels can be incorporated into a variety of techniques, e.g., splitting a sample into multiple chambers or samples or combining or mixing multiple samples together as briefly outlined above. Many variations of micro channel configurations can be designed for a particular need. The following examples illustrate some of the designs that are quite useful.

EXAMPLE 1

Use of Passive Valves in Micro Channels to Mix Samples

FIGS. 2A–L illustrate the use of stopping means in microchannels to regulate the flow of fluid through the channels. In FIG. 2A, fluid in the main channel encounters stopping means "a," causing the flow to be diverted into channel 2. In FIG. 2B, the fluid in channel 2 encounters stopping means "b" which has a greater pressure barrier than stopping means "a." As a result, the fluid flow is stopped by stopping means "b" and the fluid is forced past stopping means "a" into channel 1. FIG. 2C illustrates the fluid in channel 1 at the timepoint at which it reaches stopping means "b." This causes the wetting of all surfaces on all sides of stopping means "b." The meniscus that had been present at stopping means "b" disappears, thereby allowing fluid to freely pass stopping means "b." In FIG. 2D, flow proceeds in both channels 1 and 2 without obstruction.

This example shown in FIGS. 2A–L shows a method by which two fluids can be mixed after insertion into a set of microchannels via a single microchannel. The example shows a first fluid inserted first into a main channel. A precisely measured amount of this first fluid can be inserted into the main channel. Following insertion of the first fluid, a second fluid is inserted into the main channel behind the first fluid. This second fluid forces the first fluid along the main channel until stopping means "a" is reached. The first fluid is forced by this stopping means into channel 2. Once channel 2 is filled and the first fluid reaches stopping means "b," flow through channel 2 is stopped because stopping means "b" has a greater pressure barrier than stopping means "a." The force of the fluid in the main channel then forces the second fluid (all of the first fluid in this example having entered channel 2) past stopping means "a." When the second fluid reaches the point of stopping means "b" the pressure barrier of stopping means "b" is overcome due to the wetting of both sides of stopping means "b" and the removal of the meniscus which had originally formed at this point. At this point fluid will flow through channels 1 and 2 according to their respective impedances, and the first fluid that was in channel 2 will mix with the second fluid which was in channel 1, this mixing, occurring in channel 1 subsequent to stopping means "b."

FIG. 2E illustrates the geometry and position of the stopped fluid if stopping means "a" were that of a hydrophobic restriction. FIG. 2F illustrates the geometry and position of the stopped fluid if stopping means "b" were that of a hydrophobic restriction. FIG. 2G illustrates the geometry and position of the stopped fluid if stopping means "a" were that of a hydrophilic restriction. FIG. 2H illustrates the geometry and position of the stopped fluid if stopping means "b" were that of a hydrophilic restriction. FIG. 2I illustrates the geometry and position of the stopped fluid if stopping means "a" were that of a hydrophobic patch or a film of salt. FIG. 2J illustrates the geometry and position of the stopped fluid if stopping means "b" were that of a hydrophobic patch of greater contact angle than that of "a," or a film of salt that generates a greater surface tension in the fluid than that of "a." FIG. 2K illustrates the geometry and position of the stopped fluid if stopping means "a" were that of a passive fluid flow barrier formed by abruptly widening channel 1, wherein channel 1 and the passive fluid flow barrier is shown to be of hydrophilic construction. FIG. 2L illustrates the geometry and position of the stopped fluid if stopping means "a" and stopping means "b" were that of a passive fluid flow barrier, here shown united into a single chamber of hydrophobic construction.

The example of mixing fluids as illustrated by FIGS. 2A–L is a very simple model. More complex models in which more channels are involved could be utilized to mix more than two fluids together or to mix two fluids at one timepoint and other fluids at later timepoints, e.g. by having further branches similar to channel 2 farther downstream. The fluids that are inserted into the main channel can be inserted by several means. The main channel can encompass a single port into which all fluids are inserted or it can encompass multiple ports through which fluids can be inserted. The volume of fluids inserted can be matched with the volumes of channels to yield precise filling of channels and proper mixing of the fluids.

EXAMPLE 2

Filling of Multiple Channels or Chambers with a Single Fluid

Another example of utilizing passive valves is in a network of parallel daughter channels that flow through a set of parallel wells or chambers. The goal in this case is for a fluid or sample to be evenly distributed across all channels, and for all of the wells or chambers to fill simultaneously, and for the fluid in the wells or chambers to stop in the wells or chambers and not to continue flowing into the well or chamber outlet channel until desired. Once it is desired for the fluid to continue flowing, it is desired that the fluid flow equally further down the fluid circuit, and equally into another set of chambers or wells, if present. This is performed automatically due to passive fluid dynamics. As fluid in the main channel flows toward the parallel daughter channels and wells or chambers, imperfections in the channel walls may encourage increased flow in one channel over another. The channel with increased flow will reach the well or chamber and fill up before its sister wells or chambers are filled. However, stopping means located at strategic points in the branching daughter channels will allow fluid to fill the branching channels and catch up and stop at each generation of stopping means before proceeding further down the fluid circuit. Each generation of stopping means will need to have a greater pressure barrier than the previous generation, in order to ensure the fluid does not pass one stopping means in one branch without first catching up to that generation of stopping means in all branches. In order to ensure each well or chamber is equally filled the wells or chambers are designed with stopping means at their outlets. Because it requires greater pressure for the fluid in the filled well or chamber to go through the stopping means, the increased pressure that is generated will push the fluid in the remaining channels to cause them to overcome any small wall imperfection and catch up to the fluid that is already in the well or chamber. Hence, the stopping means acts as a passive valve and allows for an even division of fluid from a single channel into several daughter channels. It also allows for a specific sample in a main channel to be evenly distributed across a network of channels. The relative structures of the stopping means will depend on the materials, the fluid, and the pressure that is required to push the fluid past any imperfections and into all the channels, wells or chambers.

Figure 3A:
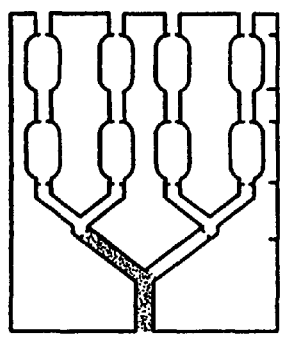
FIGS. 3A–I illustrate a method of splitting a fluid into a series of daughter channels. The filling of all sister wells or chambers prior to fluid flowing beyond the wells or chambers is controlled by stopping means at the far end of each well or chamber.
Figure 3B:
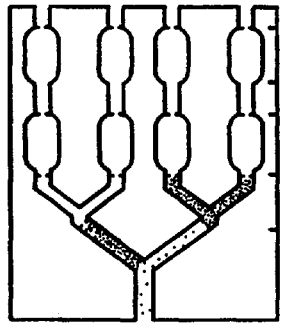
Figure 3C:
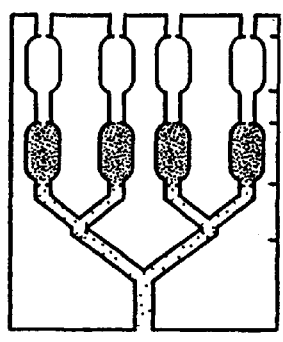
Figure 3D:
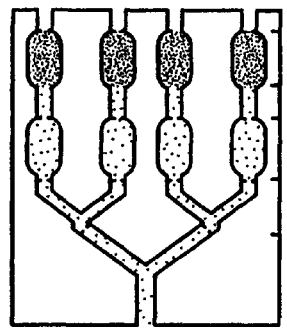
Figure 3E:
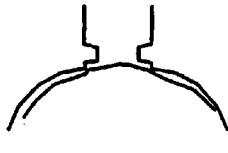
Figure 3F:
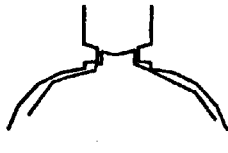
Figure 3G:
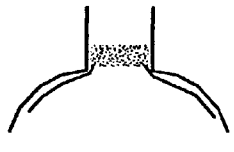
Figure 3H:
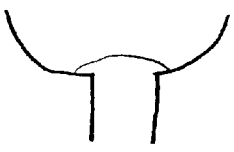
Figure 3I:
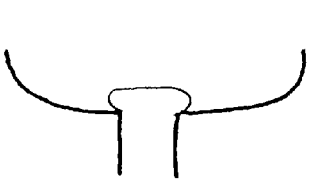

FIGS. 3A–I illustrate the effect of imperfections in microchannels and the use of stopping means to overcome problems that could have been caused by the imperfections. It also illustrates how a sample in a main channel can be evenly distributed across multiple daughter channels. In FIG. 3A fluid in one branch encounters less friction and travels further than fluid in another branch, but is stopped at the first generation of stopping means. FIG. 3B illustrates the distribution of fluid and sample as the fluid in one set of branches reach the second generation of stopping means. FIG. 3C shows that the stopping means at the outlet of the wells or chambers allow all chambers to be filled, as the back pressure generated by these stopping means causes the fluid in all the branches to push past any previous stopping means and fill the chambers equally. FIG. 3D shows that once all wells or chambers are filled, and the desired processing in the wells or chambers is completed, fluid can be pushed out of wells or chambers, through the outlet channels, and further down the fluid circuit until the next generation of stopping means are encountered. In FIGS. 3A–D the dark fluid is a sample and the lighter fluid is the system fluid. Ticks at the bottom of each figure represent the positions of the various generations of stopping means. FIG. 3E illustrates the geometry and position of the stopped fluid if the stopping means were that of a hydrophobic restriction. FIG. 3F illustrates the geometry and position of the stopped fluid if the stopping means were that of a hydrophilic restriction. FIG. 3G illustrates the geometry and position of the stopped fluid if the stopping means were that of a hydrophobic patch or a film of salt. FIG. 3H illustrates the geometry and position of the stopped fluid if the stopping means were that of a hydrophilic passive fluid flow barrier in the form of an opening into a chamber or well. FIG. 3I illustrates the geometry and position of the stopped fluid if the stopping means were that of a hydrophobic passive fluid flow barrier in the form of an opening into a chamber or well.

It is also clear to one of skill in the art that the apparatus shown in FIGS. 3A–I need not be limited to 8 wells or chambers, rather many more wells or chambers could be present. Furthermore, there is no need for the wells or chambers to all be of the same size. This makes the division of a single sample injected at point "a" into many separate wells or chambers a very simple matter. Many reaction wells or chambers can be filled without the need for pipetting individually into each well or chamber. Rather the sample is simply inserted into the apparatus at point "a" and the microchannels and physical forces involved result in the filling of all wells or chambers.

EXAMPLE 3

Use of an Air Duct in a Microfluidic Circuit

Another application of a stopping means is that of an air escape duct. In a hydrophobic material utilizing a narrow channel as a stopping means it takes a considerable amount of pressure to force fluid into an extremely small channel or duct (on the order of a few microns in diameter). Because of this water will easily flow by such a duct and continue down the channel it is in and not enter the duct. Air, on the other hand, will have no difficulty moving through the duct if its path in the fluid is restricted. This fact allows a method of releasing air bubbles that might be trapped within a fluid channel. A similar air escape duct can be fabricated in hydrophilic materials using a restriction and then a widening of the channel, or by utilizing a hydrophobic or salt patch.

Figure 4D:
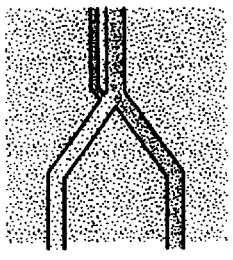
Figure 4C:
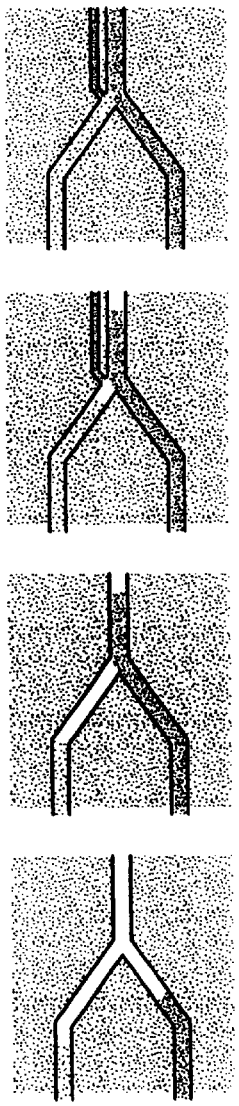
Figure 4G:
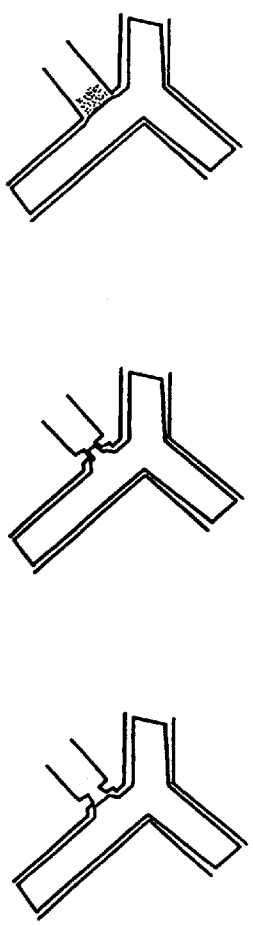
Figure 4E:
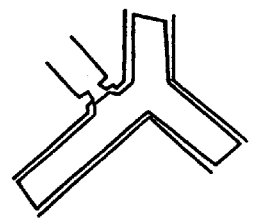

FIG. 4A shows fluid traveling down two channels that join together. FIG. 4B shows the fluid in the lower channel reaching the intersection before the fluid in the upper channel. In such an event an air bubble will trap the fluid in the upper channel and prevent the fluid in that channel from traveling further. FIG. 4C illustrates how this can be overcome by the addition of an air escape duct. In this case, fluid in the upper channel can continue to flow as the air bubble travels out of the channel into the air duct. In this illustration the air duct is represented by a long narrow channel, as might be indicative of a stopping means in a hydrophobic material. FIG. 4D illustrates fluid in both channels combining into the single channel and continuing to travel down the fluid circuit. FIG. 4E illustrates the geometry and position of the stopped fluid if the stopping means were that of a hydrophobic restriction, rather than a hydrophobic long narrow channel. FIG. 4F illustrates the geometry and position of the stopped fluid if the stopping means were that of a hydrophilic restriction. FIG. 4G illustrates the geometry and position of the stopped fluid if the stopping means were that of a hydrophobic patch or a film of salt.

Another application of an air escape duct is to allow air to escape a fluidic circuit as fluid fills the circuit. This is usually done by having air escape ducts at the endpoint in a fluid circuit, which would allow air to escape the enclosed system. This utilization of air escape ducts are depicted in FIGS. 5A–D, FIG. 6, FIGS. 8A–C, and FIGS. 10A–C, which are described in greater detail in the following Examples.

EXAMPLE 4

Consolidation of Fluids

Consolidation is the case where the contents of two or more channels or wells are to be combined into a fewer number of channels or wells. An example would be when 4 separate nucleic acid sequencing reactions are performed and then it is desired to combine the 4 reactions into a single well to be run on a gel or other analytical device. Four somewhat different consolidation methods are set out in this example.

A) Two Fluid Narrow Channel Method

This method uses two fluids with a more viscous fluid being used to force a less viscous fluid through microchannels into a chamber or well to combine the less viscous fluid from multiple chambers or wells into a fewer number of chambers or wells. This method is illustrated by FIGS. 5A–D.

Figure 5D:
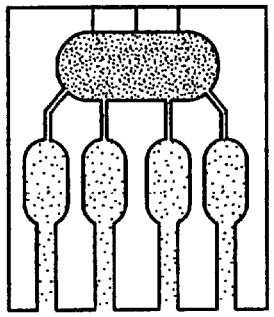
FIGS. 5A–D illustrate a two-fluid, narrow-channel method of consolidating fluid from multiple chambers into one chamber.
Figure 5C:
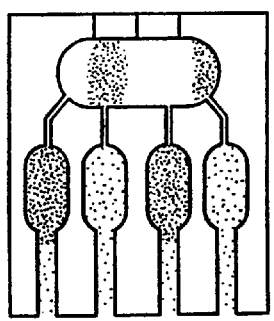
Figure 5B:
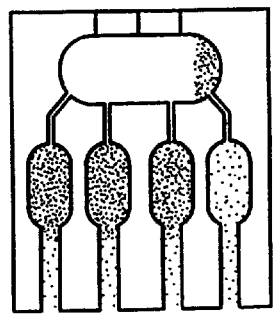
Figure 5A:
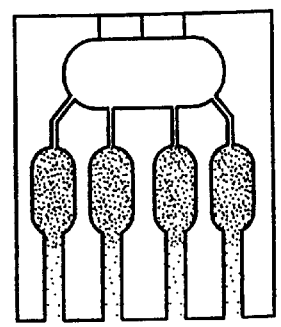

The channel or wells to be joined are filled with a fluid. The outlet of the wells or channels contains stopping means used to contain the fluid at that point in the fluid circuit. At some point upstream there is a second fluid that is more viscous than the first. There are narrow channels that connect the stopping means of the channels or wells to the point of joining. The first fluid is stopped at the stopping means (FIG. 5A). As the second viscous fluid advances down a channel it will force the first fluid through the stopping means into the narrow channel and into the point of joining or consolidation chamber (FIG. 5B). When the second fluid reaches the stopping means it does not stop because the fluid meniscus is gone. However, the pressure required to force the more viscous solution through the narrow channel is instead used to push the first fluid in a neighboring channel into the point of joining (FIG. 5C). This process is repeated until all wells or channels are emptied of the first fluid and the pumping is stopped (FIG. 5D). FIGS. 3E–I illustrate the possible geometries and positions of the stopped fluid if the stopping means at the outlet of the channels or wells were that of a hydrophobic restriction, a hydrophilic restriction, a hydrophobic patch, a salt film, and a passive fluid flow barrier such as an entrance into a chamber from a hydrophilic or hydrophobic microchannel, respectively. If the material were hydrophobic, only a long narrow channel would be needed, rather than both a restriction and then a long narrow channel. The utilization of air escape ducts at the consolidation chamber would be similar to those depicted in Example 3 and FIGS. 4E–G.

Figure 6:
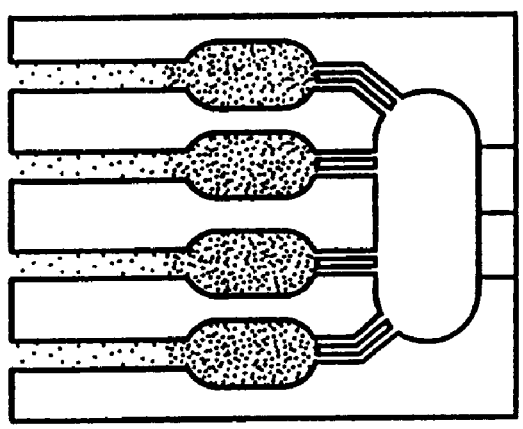
FIG. 6 illustrates a two-fluid, narrow-channel method of consolidating fluid from multiple chambers into one chamber wherein multiple narrow connecting channels connect the stopping means of each of the multiple chambers to the consolidation chamber.

Since the narrow connecting channels are very small there is a high chance of them becoming occluded by small particles. To reduce this risk redundant channels may be made. This is illustrated by FIG. 6. This will help ensure the likelihood of an open channel being present to allow proper consolidation.

B) Joining Channel with Restriction and Air Escape Vent Method

Figure 7A:
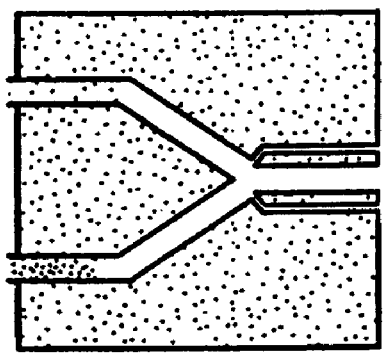
FIGS. 7A–D illustrate the concept of using air escape vents in conjunction with each of two channels wherein each of the channels comprises a stopping means.
Figure 7B:
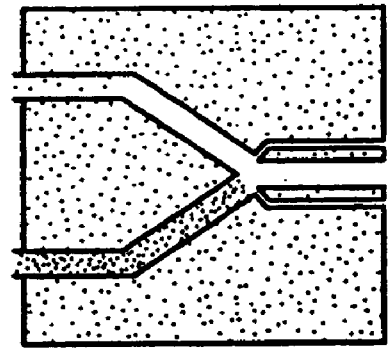
Figure 7C:
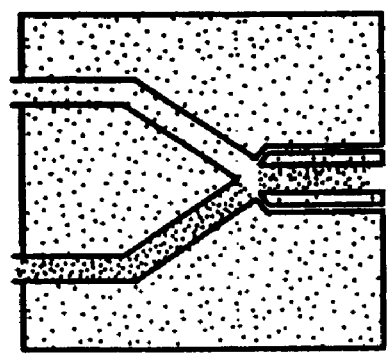
Figure 7D:
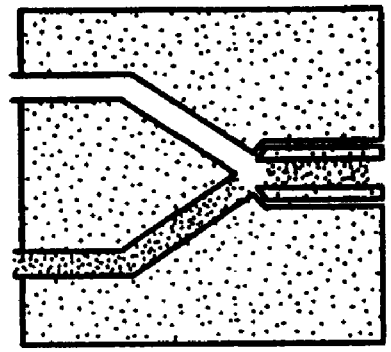

The concept of having an air escape vent present to allow the release of what normally would be a trapped bubble is discussed above in Example 3. A variation is shown here in a method of consolidation wherein stopping means are present (see FIGS. 7A–D). FIG. 7A shows two fluids each entering a channel. Each channel has a stopping means at the point where the two channels on the left join to become a single channel. This allows the fluid in both channels to catch up to themselves at the point where the channels join (FIG. 7C). The presence of an air vent in each of the two initial channels ensures that neither channel will have an air lock and both will advance to the joining region. Once one fluid breaks through its stopping means it will wet the other surface of the stopping means in the neighboring channel, eliminating its meniscus. This will allow both fluids to flow into the joining channel and mix together (FIG. 7D). Structure and position of fluid in the stopping means and air escape ducts have been shown in FIGS. 2E–J and 4E–G.

C) Air Displacement Method

Figure 8C:
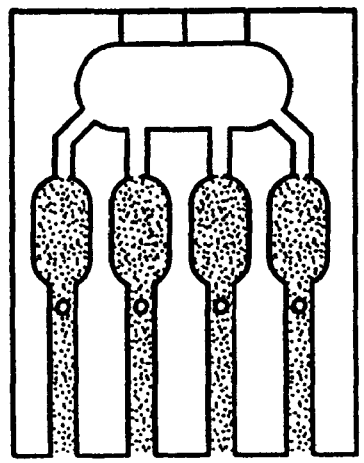
FIGS. 8A–C illustrate the use of ports to allow the introduction of air, another gas, or a second fluid to be introduced to force fluids past a stopping means.
Figure 8B:
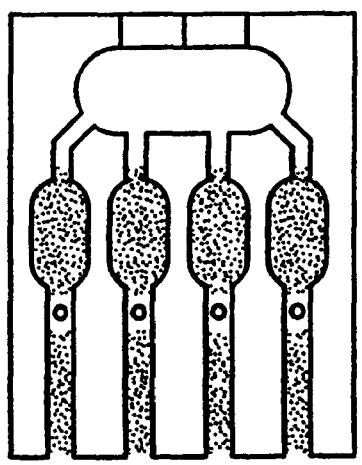
Figure 8A:
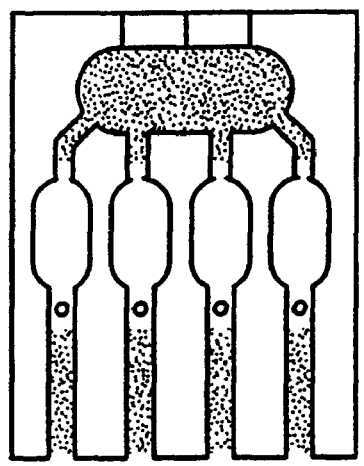

Another method of consolidation requires the use of ports coming from a third dimension, e.g., from above or below. The ports possess stopping means at their connection point to the fluid channel so that, under normal operating pressures, fluid will not flow into them. Fluid flows into wells or channels and is stopped at a known location due to the use of stopping means (in the circuit of FIG. 8A, stopping means exist at the right of each of the 4 initial wells between each well and the exiting microchannel). Air or another gas is pushed through the ports (appearing as holes to the left of the 4 initial wells in FIGS. 8A–C) into the fluid channels. The air will displace the fluid downstream past the stopping means (FIG. 8B), and in this case, into the consolidation well (FIG. 8C). Air escape ducts in the consolidation well allow displaced air to exit the system so fluid can fill the consolidation well. A second fluid, rather than air, could also be pushed through the ports and used to displace the well volumes into the consolidation chamber.

D) Physical Displacement Method

Figure 9A:
FIGS. 9A–D illustrate a physical displacement method in which pressure is applied to a flexible region of a circuit thereby forcing the fluid in the circuit to be moved.
Figure 9B:
Figure 9C:
Figure 9D:

This method also requires the use of a third dimension. In this case a portion, preferably the top or bottom, of the fluid circuit is made to be flexible at the point where physical displacement is to occur. The top or bottom plate has an opening that can allow a displacement means to compress the flexible fluid circuit to push fluid further downstream. This displacement means can be a fluid such as water, a gas such as air, or a plunger of some kind. This is illustrated in FIGS. 9A–D. FIG. 9A shows an empty circuit. FIG. 9B shows the circuit partially filled with fluid. The bottom of the wells is made of a flexible material. In this example, a displacement means (water) is introduced below the last well filled with fluid. The water compresses the bottom of the well (FIG. 9C) forcing the fluid from the well into the neighboring empty well (FIG. 9D). The displacement means can be introduced elsewhere and need not be directly at the last filled well.

EXAMPLE 5

Modified Two Fluid Narrow Channel Methods of Consolidation

Figure 10A:
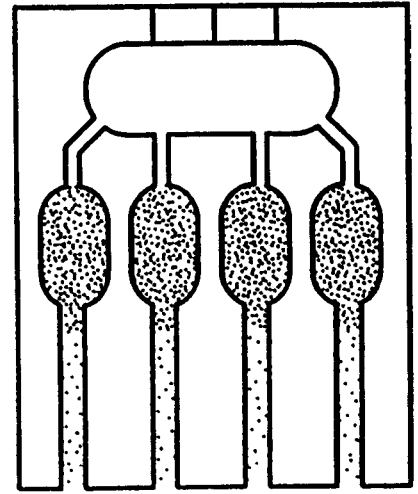
FIGS. 10A–C illustrate three versions of a consolidation circuit.
Figure 10B:
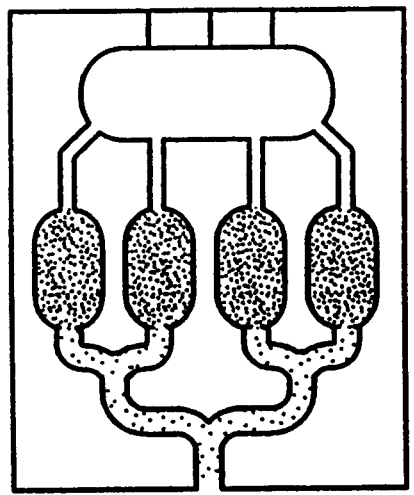
Figure 10C:
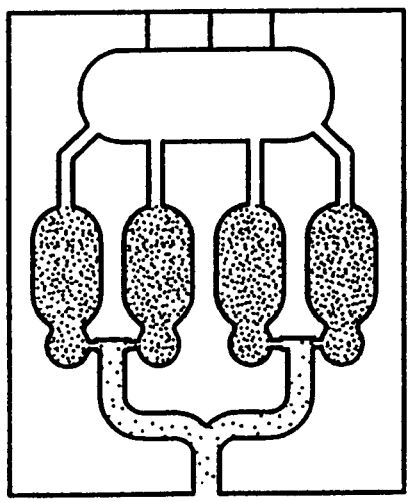

The method described above in Example 4, Section A, and illustrated in FIGS. 5A–D has been modified to yield improved results. Two modifications are illustrated in FIGS. 10B–C with FIG. 10A showing the original design for comparison. The design shown in FIG. 10B incorporates stopping means just upstream of each of the four wells. The stopping means illustrated are microchannel narrowings, but may alternatively be passive fluid flow barriers such as abrupt microchannel widenings, or an inlet into the well or chamber itself. These stopping means facilitate an even distribution of a sample into each of the channel branches leading to the four wells. Although not illustrated in FIG. 5A or 10A, the 4 channels leading to the wells could have branched off from a single source or alternatively could have come from 4 different sources.

In practice the design of FIG. 10B does not work very well. This is because hydrophobic or hydrophilic restrictions act as jet nozzles pushing the second, more viscous fluid into the first fluid and causing unwanted mixing. This results in consolidation that is less than optimum and a fair amount of the second solution is found in the large consolidation well at the right in FIG. 10B. Although this is useful as a mixing method, it is not the desired result in this case.

FIG. 10C illustrates a modification of the consolidation design that eliminates the unwanted mixing seen with the design shown in FIG. 10B. The entrance channel is put on the side of the well and the well is shaped somewhat in the form of a bowling pin where one bulb or section is significantly larger than the other section and the channel joining the two is not necessarily narrow and sharp. This allows the velocity of the second fluid to slow down and stabilize in the small first section before it interacts with the bulk of the first fluid in the large second section. If the transition between the first and second sections is smooth and gradual the second fluid (if properly chosen) will remain intact with itself and there will be a clear division between the first and second fluids as the second fluid fills the well and forces the first fluid through the narrow channel into the consolidation well. The stopping means used in FIG. 10A are suitable for use in the refinement shown in FIG. 10B.

EXAMPLE 6

Temporarily Bypassing a Fluid Circuit Section

Example 1 illustrated the use of stopping means to divert fluid from one path to a branching path of a microfluidic circuit. Example 3 illustrated the use of air escape ducts to allow what would normally be trapped air to escape a channel and allow fluid to flow through the channel and eventually combine with the fluid in a joining channel. Utilizing these techniques a fluid circuit section can be temporarily bypassed using stopping means that divert fluid into a different path. A downstream stopping means can be used to overcome the pressure barrier at the original stopping means, and then an air escape duct can be used to allow fluid to flow through the bypassed region and rejoin the fluid circuit from which it had been cut off.

Figure 11A:
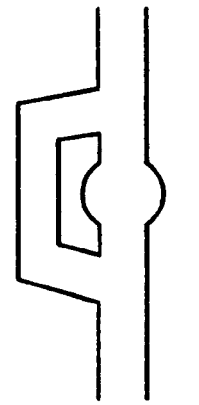
FIGS. 11A–E illustrate the combination of stopping means and air escape vents to allow fluid to bypass a particular fluid circuit section. The bypassed region can be later perfused by a downstream stopping means generating enough backpressure to overcome the original stopping means that prevented flow into the non-perfused region.
Figure 11B:
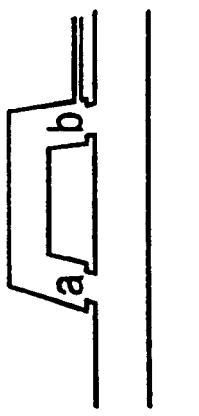
Figure 11D:
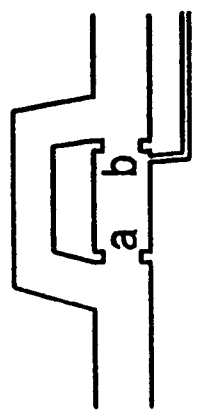
Figure 11C:
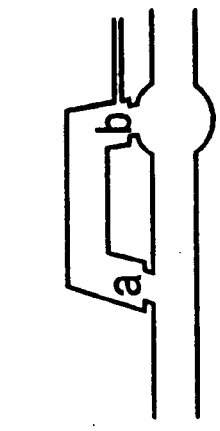
Figure 11E:
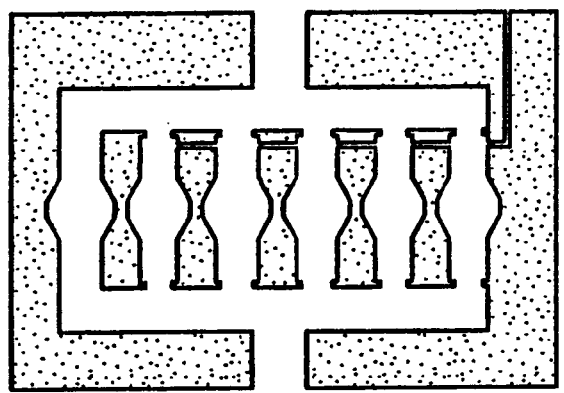

FIGS. 11A–E illustrate this technique. In FIG. 11A fluid flows down a main channel and encounters a stopping means "a" that diverts the flow into a side channel. When the side channel rejoins the main channel it is prevented from entering the bypassed region of the main channel because of a second stopping means "b" that diverts the fluid to flow further down the main channel. At some point downstream another stopping means with a greater pressure barrier than the original stopping means "a" causes fluid to push past stopping means "a." An air escape duct located at the upstream side of stopping means "b" allows fluid to flow through the main channel. When it reaches stopping means "b" the meniscus disappears and the pressure barrier at stopping means "b" is eliminated. Fluid can then flow through both the main channel and side channel according to their respective impedances. It is important that the pressure barrier at stopping means "b" is greater than the pressure barrier at stopping means "a" to ensure fluid does not push past stopping means "b" before it pushes past stopping, means "a." FIG. 11B illustrates a similar situation, except where fluid in a main channel is prevented from entering a side channel due to stopping means at "a" and "b." FIG. 11C illustrates a chamber or well in the fluid circuit that may be bypassed initially, or perfused initially, depending on the location of the stopping means and air escape ducts. FIG. 11D illustrates a chamber that is located at the point of joining of two channels, where one inlet to the chamber is a bypassed branch from the main channel. FIG. 11E illustrates a main channel that includes a chamber, and a series of secondary channels that contain chambers and that are bypassed, all of which contain stopping means to prevent their perfusion, and air escape ducts that allow their ultimate perfusion. The stopping means at the upstream positions of the secondary channels are designed such that their pressure barriers can be overcome in the sequence that is desired, in this illustration from the top to the bottom, for the fluid circuit to function properly. The air escape ducts can either sequentially lead to the secondary channels that are not yet perfused, or can lead to the outside via ducts traveling in a third dimension.

The above examples demonstrate methods of diluting or mixing two fluids traveling beside one another in a single channel, methods of allowing branching channels to divide flowing fluid, methods of allowing air to escape out of a fluid circuit, methods of consolidating channels or samples, and methods of temporarily bypassing a fluid path, all using passive fluid dynamics based on pressure barriers created by manipulating fluid capillary forces.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

U.S. Pat. No. 4,946,795
U.S. Pat. No. 5,119,116
U.S. Pat. No. 5,498,392
U.S. Pat. No. 5,587,128
U.S. Pat. No. 5,627,041
U.S. Pat. No. 5,726,026
R. C. Anderson et al., "Microfluidic biochemical analysis system," Int. Conf. On Solid-State Sens and Act, Transducers '97, p477–80 (1997).
S. N. Brahmasandra et al., "A microfabricated fluidic reaction and separation system for integrated DNA analysis," Micro Total Analysis Systems '98, D. J. Harrison and A Van den Berg, eds., p267–70. Kluwer Acad. Publ., Dordrecht (1998).
K. Hosokawa et al., "Hydrophobic microcapillary vent for pneumatic manipulation of liquid in $\mu$TAS," Micro Total Analysis Systems '98, D. J. Harrison and A Van den Berg, eds., p307–10, Kluwer Acad. Publ., Dordrecht (1998).
P. F. Man et al., "Microfabricated capillarity-driven stop valve and sample injector," IEEE $11^{th}$ Annual Int. MEMS Workshop, p. 45–50 (1998).

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A method for consolidating fluids from multiple microfluidic channels into a common consolidation well, chamber or channel, comprising the steps of:
   c. injecting fluids into multiple microchannels of a microfluidic circuit; then
   d. applying pressure to fluid in each of said multiple microchannels sufficient to force said fluid through said microchannels until it stops at a passive fluid flow barrier formed at the junction of each of said microchannels with the common consolidation well, chamber or channel whereby fluid reaches but does not pass each passive fluid flow barrier; and then
   e. applying further pressure to fluid in each of said multiple microchannels sufficient to overcome said passive fluid flow barriers and permit said fluid to enter said common consolidation well, chamber or channel from each of said multiple microchannels;
wherein said passive fluid flow barrier formed at the junction of each said microchannel with the common consolidation well, chamber or channel is sufficient to at least temporarily block the flow of fluid in said microchannel.

2. The method of claim 1, wherein at least one said passive fluid flow barrier is an abrupt channel widening having an inlet radius equal to the channel radius and an outlet radius equal to the radius of the consolidation chamber.

3. A non-wetted fluid circuit comprising a plurality of connected microchannels, wherein an abrupt microchannel widening is present within one or more of said microchannels, said widening having an inlet radius and an outlet radius, wherein said outlet radius is sufficiently larger than said inlet radius to create a passive fluid flow barrier sufficient to cause fluid which is advancing through said fluid circuit to flow preferentially in an adjoining microchannel connected upstream of said widening rather than to flow past said widening.

4. The fluid circuit of claim 3, wherein said microchannels form a tree-like or fractal branching.

5. The fluid circuit of claim 4, wherein said microchannels connect to one or more chambers or wells.

6. A non-wetted fluid circuit comprising a plurality of connected microchannels, wherein a passive fluid flow barrier exists within at least one of said microchannels, wherein said passive fluid flow barrier comprises an inlet having a radius $r_1$ and an outlet having a radius $r_2$, wherein $r_1$ is sufficiently smaller than $r_2$ to create a passive pressure barrier causing fluid that is advancing through said fluid circuit to flow into an adjoining microchannel connected upstream of said passive fluid flow barrier rather than to flow past the passive fluid flow barrier, and wherein said passive pressure barrier is sufficient to at least temporarily block the flow of fluid in said at least one microchannel.

7. The non-wetted fluid circuit of claim 6, wherein at least one said microchannel comprises a chamber.

8. The non-wetted fluid circuit of claim 6, wherein radius $r_1$ is from about 0.1 to about 5000 $\mu$m in size.

9. The non-wetted fluid circuit of claim 6, wherein radius $r_1$ is from about 0.1 to about 1000 $\mu$m in size.

10. The non-wetted fluid circuit of claim 6, wherein radius $r_2$ is greater than about 1.5 times radius $r_1$.

11. The non-wetted fluid circuit of claim 6, wherein radius $r_2$ is greater than about two times radius $r_1$.

12. The non-wetted fluid circuit of claim 6, wherein radius $r_2$ is greater than about three times radius $r_1$.

13. The non-wetted fluid circuit of claim 6, wherein radius $r_2$ is greater than about five times radius $r_1$.

14. The non-wetted fluid circuit of claim 6, wherein radius $r_2$ is greater than about ten times radius $r_1$.

15. The non-wetted fluid circuit of claim 6 wherein said non-wetted fluid circuit comprises secondary microchannels that include passive fluid flow barriers that create passive pressure barriers to fluid advancing through the fluid circuit.

16. The non-wetted fluid circuit of claim 15 wherein said passive flow barriers are of different strengths, wherein a weaker passive flow barrier will be overcome before a stronger passive flow barrier, and wherein a microchannel downstream of a weaker passive flow barrier will fill before a microchannel downstream of a stronger passive flow barrier.

17. The non-wetted fluid circuit of claim 16 wherein the strengths of said passive flow barriers are selected to determine the order in which said secondary microchannels will fill.

18. The non-wetted fluid circuit of claim 15 wherein one or more of said secondary microchannels comprises a vent.

19. The non-wetted fluid circuit of claim 6 wherein said microchannels form a treelike or a fractal branching.

20. The non-wetted fluid circuit of claim 6 wherein said passive fluid flow barrier comprises a hydrophilic surface.

21. The non-wetted fluid circuit of claim 6 wherein said passive fluid flow barrier comprises a hydrophobic surface.

22. The non-wetted fluid circuit of claim 6 wherein said passive fluid flow barrier comprises a hydrophilic surface.

23. A non-wetted fluid circuit comprising a plurality of connected microchannels, wherein a first passive fluid flow barrier exists within at least one of said microchannels, and wherein said first passive fluid flow barrier comprises an inlet having a radius $r_1$ and an outlet having a radius $r_2$, wherein $r_1$ is sufficiently smaller than $r_2$ to create a passive pressure barrier causing fluid that is advancing through said fluid circuit to flow in an adjoining microchannel connected upstream of said first passive fluid flow barrier rather than to flow past said first passive fluid flow barrier, wherein at least one of said microchannels branches at a first point into an adjoining microchannel which rejoins said one of said microchannels at a second point and wherein said adjoining microchannel comprises a second passive fluid flow barrier immediately upstream of said second point, wherein said first passive pressure barrier is sufficient to at least temporarily block the flow of fluid in said at least one microchannel, and wherein said second passive fluid flow barriers is sufficient to at least temporarily block the flow of fluid in said adjoining microchannel.

24. The non-wetted fluid circuit of claim 23, wherein said microchannels form a treelike or a fractal branching.

25. The non-wetted fluid circuit of claim 23, further comprising one or more ports allowing a gas to enter into said fluid circuit.

26. The non-wetted fluid circuit of claim 25 wherein said ports are large enough to allow gas to pass through said ports but small enough to prevent fluids from passing through said ports at a specific operating pressure.

27. The non-wetted fluid circuit of claim 23 further comprising one or more ports through which a fluid under pressure may enter into said fluid circuit.

28. A method of moving a first fluid through the fluid circuit of claim 22, comprising the steps of:
   a. injecting a first fluid under pressure into said fluid circuit via said one or more ports; and
   b. forcing a second fluid under pressure through said one or more ports, said second fluid thereby forcing said first fluid to move through said fluid circuit.

29. The non-wetted fluid circuit of claim 23 wherein the fluid circuit comprises one or more wells or chambers joined to a common consolidation well or chamber by one or more microchannels.

30. A non-wetted fluid circuit comprising a first microchannel and a second microchannel wherein said second microchannel branches from said first microchannel at a first intersection and rejoins said first microchannel at a second intersection, wherein said second microchannel has a first passive fluid flow barrier comprising a first abrupt microchannel widening at said first intersection and a second passive fluid flow barrier comprising a second abrupt microchannel widening at said second intersection, wherein said second passive fluid flow barrier creates a greater pressure barrier than said first passive fluid flow barrier, wherein said first passive fluid flow barrier is sufficient to at least temporarily block the flow of fluid in said second microchannel, wherein said second passive fluid flow barrier is sufficient to at least temporarily block the flow of fluid in said second microchannel, and wherein said fluid circuit further comprises a vent between said first passive fluid flow barrier and said second passive fluid flow barrier.

31. The fluid circuit of claim 30 wherein said first abrupt microchannel widening comprises a chamber or well between said first intersection and said second intersection.

32. The fluid circuit of claim 30 wherein said second abrupt microchannel widening comprises a chamber or well at said second intersection.

33. A method of controlling fluid flow through a non-wetted fluid circuit comprising at least two connected microchannels, each said microchannel containing a passive fluid flow barrier that creates a fluid pressure barrier, said method comprising:
   advancing fluid in a first microchannel until it is stopped by the fluid engaging a first passive fluid flow barrier;
   advancing fluid in a connected neighboring second microchannel until it reaches a second passive fluid flow barrier; and
   overcoming the pressure barrier of one of said first and second passive fluid flow barriers by the fluid engaging the other of said first and second passive fluid flow barriers and with the application of sufficient pressure to the fluid;
   wherein said first passive fluid flow barrier is sufficient to at least temporarily block the flow of fluid in said first microchannel, wherein said second passive fluid flow barrier is sufficient to at least temporarily block the flow of fluid in said second microchannel, wherein one of said first and second passive fluid flow barriers creates a weaker pressure barrier than the other said passive fluid flow barrier, wherein said weaker barrier is overcome first, and wherein at least one of said passive fluid flow barriers is an abrupt microchannel widening.

34. The method of claim 33, wherein fluid is directed into a connected neighboring second microchannel as a consequence of said fluid engaging said first passive fluid flow barrier in said first microchannel.

35. The method of claim 33, wherein said abrupt microchannel widening is selected from the group consisting of chambers, wells, long channel widenings, and short channel widenings.

36. The method of claim 33 wherein each of said first passive fluid flow barrier and said second passive fluid flow barrier is a capillary barrier having an inlet and an outlet, and wherein the outlet is sufficiently larger than the inlet to create the fluid pressure barrier of the passive fluid flow barrier.

37. The method of claim 36, wherein the outlet of each of the first and the second passive fluid flow barriers is defined by a radius $r_2$ which is at least about two times the size of a radius $r_1$ which defines the inlet of each of the first and the second passive fluid flow barriers.

38. The method of claim 36, wherein the outlet of each of the first and the second passive fluid flow barriers is defined by a radius $r_2$ that is at least about five times the size of a radius $r_1$ that defines the inlet of each of the first and the second passive fluid flow barriers.

39. The method of claim 33 wherein the second microchannel branches from the first microchannel at a point immediately upstream of the first passive fluid flow barrier.

40. The method of claim 33 wherein the first and second passive fluid flow barriers each comprise an opening into a well or chamber.

41. The method of claim 33 wherein the fluid circuit comprises one or more wells or chambers joined to a common consolidation well or chamber by one or more microchannels.

42. The method of claim 33 wherein the fluid circuit comprises one or more air vents.

43. A method of mixing a first fluid and a second fluid within a non-wetted fluid circuit, said method comprising the steps of
   inserting said first fluid into a main microchannel of said fluid circuit, wherein said first fluid is forced to flow into a first microchannel of said circuit of a known volume by a first abrupt microchannel widening within said main microchannel, and wherein said first microchannel comprises a second abrupt microchannel widening that creates a pressure barrier stronger than said first abrupt microchannel widening, wherein said first fluid is of all amount substantially equal to the volume of said first microchannel, and
   inserting said second fluid into said main microchannel of said fluid circuit, wherein said second fluid is forced past said first abrupt microchannel widening into a second microchannel, and said first microchannel and said second microchannel converge at said second abrupt microchannel widening at which point said first fluid and said second fluid will mix upon continued insertion of said second fluid or application of a force causing said first and second fluids to move;
   wherein said first abrupt microchannel widening is sufficient to at least temporarily block the flow of fluid in said main microchannel, and wherein said second abrupt microchannel widening is sufficient to at least temporarily block the flow of fluid in said first microchannel.

44. The method of claim 43, wherein said fluid circuit comprises a vent.

45. The method of claim 43, wherein said first abrupt microchannel widening and said second abrupt microchannel widening are capillary barriers selected from the group consisting of chambers, wells, long channel widenings, and short channel widenings.

46. A method of distributing fluid from one channel to multiple wells, chambers or channels of a non-wetted fluid circuit wherein said method comprises the steps of:
   passing the fluid from said one channel to branching channels leading to a first set of wells, chambers or channels, wherein said first set of wells, chambers or channels comprises a first passive fluid flow barrier within each well, chamber or channel that creates a fluid pressure barrier causing fluid to fill said branching channels upstream of said first passive fluid flow barrier prior to moving to a second set of wells, chambers or channels, wherein said second set of wells, chambers or channels comprise a second passive fluid flow barrier within each well, chamber or channel that creates a fluid pressure barrier that is stronger than the fluid pressure barrier created by said first passive fluid flow barriers, wherein the first passive fluid flow barriers comprise said channel opening into said first set of wells, chambers, or channels; and causing fluid to push past the first passive fluid flow barriers within the first set of wells, chambers or channels and to stop at the second passive fluid flow barriers within the second set of wells, chambers or channels;

wherein each said first passive fluid flow barrier is sufficient to at least temporarily block the flow of fluid in the corresponding upstream branching channel, and wherein each said second passive fluid flow barrier is sufficient to at least temporarily block the flow of fluid in the corresponding upstream well, chamber or channel.

47. A microfluidic circuit comprising:

a. a plurality of microchannels; and b. a common consolidation clamber;

wherein each of said plurality of microchannels joins to said consolidation chamber at a junction; wherein said consolidation chamber has a cross sectional area substantially greater than the cross sectional area of each said microchannel; and wherein a passive fluid flow barrier is formed at the junction of each said microchannel with said consolidation chamber; wherein said passive fluid flow barrier formed at the junction of each said microchannel with the consolidation chamber is sufficient to at least temporarily block the flow of fluid in said microchannel.

48. The microfluidic circuit of claim 47, wherein at least one of said microchannels comprises a chamber.

49. A method of controlling fluid flow through a non-wetted fluid circuit comprising at least two connected microchannels, each said microchannel containing a passive fluid flow barrier that creates a fluid pressure barrier, said method comprising:

stopping advancing fluid in a first microchannel with a first passive fluid flow barrier, thereby directing fluid into a connected neighboring second microchannel, wherein said first passive fluid flow barrier comprises an inlet having a radius $r_1$ and an outlet having a radius $r_2$, wherein than $r_2$ is sufficiently larger than $r_1$ to create a passive pressure barrier causing fluid that is advancing through said fluid circuit to stop at said first passive fluid flow barrier; and overcoming the pressure barrier of the first passive fluid flow barrier by the advancing fluid engaging a second passive fluid flow barrier in the second microchannel, wherein said second passive fluid flow barrier creates a stronger pressure barrier than the first passive fluid flow barrier;

wherein said first passive fluid flow barrier is sufficient to at least temporarily block the flow of fluid in said first microchannel, and wherein said second passive fluid flow barrier is sufficient to at least temporarily block the flow of fluid in said second microchannel.

50. The method of claim 49 wherein the second passive fluid flow barrier comprises an inlet having a radius $r_1$ and an outlet having a radius $r_2$, wherein $r_2$ is sufficiently larger than $r_1$ to create a passive pressure barrier greater than the first passive fluid flow barrier.

51. The method of claim 49 wherein the second microchannel branches from the first microchannel at a point immediately upstream of the first passive fluid flow barrier.

52. The method of claim 49 wherein the fluid circuit comprises one or more wells and chambers.

* * * * *